(12) United States Patent
Hofeldt

(10) Patent No.: US 11,779,203 B1
(45) Date of Patent: Oct. 10, 2023

(54) ANIMATED STEREOSCOPIC ILLUSIONARY THERAPY AND ENTERTAINMENT

(71) Applicant: Albert John Hofeldt, Miami Beach, FL (US)

(72) Inventor: Albert John Hofeldt, Miami Beach, FL (US)

( * ) Notice: Subject to any disclaimer, the term of this patent is extended or adjusted under 35 U.S.C. 154(b) by 0 days.

(21) Appl. No.: 17/379,062

(22) Filed: Jul. 19, 2021

(51) Int. Cl.
| | |
|---|---|
| *A61B 3/032* | (2006.01) |
| *H04N 13/385* | (2018.01) |
| *H04N 13/271* | (2018.01) |
| *A61B 3/08* | (2006.01) |
| *A61H 5/00* | (2006.01) |

(52) U.S. Cl.
CPC ............. *A61B 3/032* (2013.01); *A61B 3/08* (2013.01); *A61H 5/005* (2013.01); *H04N 13/271* (2018.05); *H04N 13/385* (2018.05)

(58) Field of Classification Search
CPC ........ A61B 3/032; A61B 3/08; H04N 13/385; H04N 13/271; A61H 5/005
See application file for complete search history.

(56) References Cited

U.S. PATENT DOCUMENTS

| | | | | |
|---|---|---|---|---|
| 8,820,930 | B2 * | 9/2014 | Fateh | A61B 3/022 351/205 |
| 11,116,665 | B2 * | 9/2021 | Hess | A61F 9/00829 |
| 2007/0200927 | A1 * | 8/2007 | Krenik | A61B 3/0033 348/47 |
| 2013/0100400 | A1 * | 4/2013 | Hofeldt | A61B 3/022 351/201 |
| 2019/0014981 | A1 * | 1/2019 | Hooriani | A61B 3/0091 |
| 2021/0330185 | A1 * | 10/2021 | Krukowski | A61B 3/113 |
| 2022/0240774 | A1 * | 8/2022 | Qi | A61B 3/005 |

FOREIGN PATENT DOCUMENTS

WO WO-2017125422 A1 * 7/2017 ............... A61B 3/08

* cited by examiner

*Primary Examiner* — Collin X Beatty

(57) ABSTRACT

Illusionary motion-in-depth for vision therapy or entertainment is provided by altering the positional disparity by relative speed of movement and/or delay of movement of images of an image pair in motion which are viewed on a digital display device by stereoscopic means.

10 Claims, 8 Drawing Sheets

40

41

42

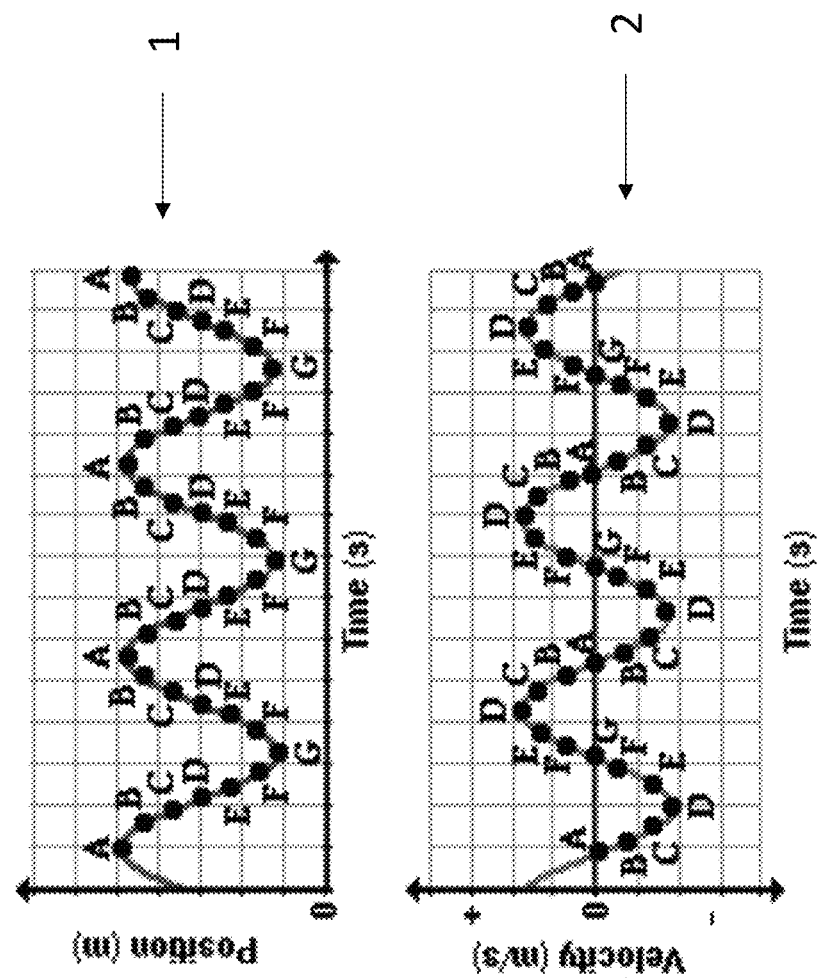
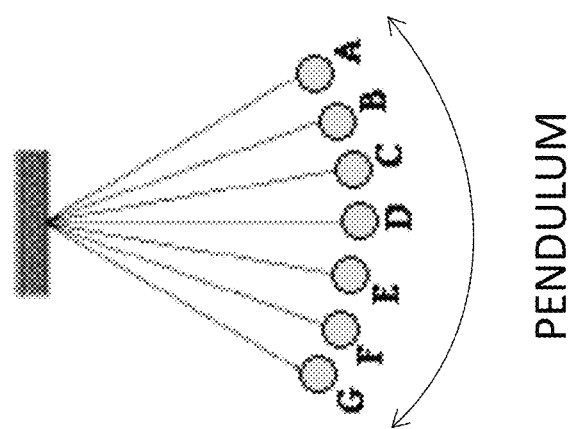
Prior Art
FIG. 1

ANIMATED STEREOSCOPIC ILLUSIONARY THERAPY AND ENTERTAINMENT

CROSS REFERENCE TO RELATED APPLICATIONS

Not Applicable

Statement Regarding Federally Sponsored Research or Development

Not Applicable

The Names of the Parties to a Joint Research Agreement

Not Applicable

Incorporated-by-Reference of Material Submitted on a Compact Disc or as a Text File Via the Office Electronic Filing System (EFS-Web)

Not Applicable

Statement Regarding Prior Disclosures by the Inventor or a Joint Inventor

Not Applicable

BACKGROUND OF THE INVENTION

Field of the Invention

This invention relates relative movement of images of an image pair and depth of stereopsis. To be more specific, this invention pertains to binocular stimulation by one or more image pairs in motion where images of the each image pair are disparate due to unequal movement delay, unequal duration of movement, or both.

Related Art

U.S. Pat. No. 11,007,109, Patent Date May 18, 2012. Binocular Amblyopic Therapy.

INTRODUCTION

Motion-in-depth is an important attribute for judging the location of moving objects. Motion-in-depth can also be illusionary which is best illustrated by the Pulfrich effect that was first described in 1922 by Carl Pulfrich, a stereoscopy expert. In the Pulfrich effect, an oscillating pendulum appears to rotate in an illusional orbit rather than move in a straight path. This illusion occurs when nerve conduction is delayed in one eye due to disease or when a neutral density filter is placed to dim one eye.-Hofeldt patent (U.S. Pat. No. 11,007,109 B1) illustrated in Prior Art (FIG. 2) teaches active therapy for amblyopia by stimulating binocular visual pathways with positional disparate fusible image pairs in-motion where a Pulfrich-like effect is perceived by a subject when the motion of the either the right or left image is delayed in time while traveling at the same speed.

In this application, I am specifying how to produce illusionary motion-in-depth of moving image pairs with positional disparity by: (1) desynchronizing the speed of the image pairs, (2) desynchronizing the speed of the image pair combined with delaying one image of the image pair, (3) desynchronizing the starting of identical movies viewed by the right and left eyes containing subject matter of images in-motion, and (4) layering disparate image pairs in-motion over desynchronized identical movies containing subject matter of images in-motion.

DETAILED DESCRIPTION OF THE INVENTION

Parameters of movement animation include (1) delay of movement, (2) duration of movement, and (3) deceleration and acceleration movement functions of "ease in", "ease out" and "ease in and out". Speed is programmed through duration of movement: to increase speed, duration is shortened and to decrease speed, duration is lengthened.

The oscillation of a pendulum as illustrated by Prior Art in FIG. 1 (www.physicsclassroom.com/class/waves/Lesson-0/Pendulum-Motion) moves along a straight path with midpoint labelled D and maximum displacements labelled G and A as depicted in graph 1. The speed of the pendulum in maximum at point D and reaches zero a points G and A as depicted in graph 2. The to and fro movement of the pendulum is smooth. This gradual natural-appearing alternating deceleration and acceleration motions of the pendulum can be applied to animate objects by using "ease in", "ease out" and "ease in and out" animation function in computer programing. Ease-in animations start slowly and end fast, which is the opposite of ease-out animations. Something in the range of 300-500 ms is typically suitable, but the exact number depends heavily on the feel of your project. (Paul Lewis, The basics of Easing, https://developers.google.com/web/fundamentals/design-and-ux/animations/the-basics-of-easing).

Hofeldt patent (U.S. Pat. No. 11,007,109 B1) as illustrated in FIG. 2 shows the Pulfrich effect in a game format where bird 4a and 4b are image pairs traveling along a circuitous path within the visual space where a delay in motion of one of the two images of the image pair produces perception of depth. Cactus 5 within the visual space is a reference point for depth perception. Hofeldt patent points out that a delay in motion between paired images produces the perception of depth, when moving along a straight path from left to right, delaying the image seen by left eye causes a posterior arching path and delaying the image seen by right eye causes an anterior arching path. Conversely, when moving along a straight path from right to left, delaying the image seen by the right eye causes a posterior arching path and delaying the image seen by the left eye causes an anterior arching path. In addition to describes moving alone a straight path, Hofeldt patent goes on to describe paired images moving along a circuitous path where paired images have both vertical and horizontal disparities and remain fused when disparities are within the fusible range. The fusible normal range entails Panum's fusional area of 6-minutes of arch, the range for fusional disparity is greater for horizontal than for vertical disparity (Fender, D., & Julesz, B. (1967). Extension of Panum's fusional area in binocularly stabilized vision. Journal of the Optical Society of America, 57(6), 819-830. https://doI.org/10.1364/JOSA.57.000819). For a bird image pair moving vertically, the tolerable disparity difference between images is less than for when the bird image pair moves in a horizontal direction before the fused image pair break fusion and are seen double.

FIGS. 3a and 3b illustrate the left to right linear unidirectional path of an image pair moving at the same speed, made up of image 21 (depicted by circled R) seen by the left eye and image 20 seen by the right eye and where the onset of motion of left image 21 (depicted by circled L) is delayed by X time. Viewing the motion from above, the arrows indicate the image pair moves clockwise as compared to reference clock 25. With onset of movement, fused image 26 appears to move backward from position A to position B due to the disparity produced by the time delay of image 21 as illustrated in FIG. 3b. The X time delay is constant as depicted by parallel time/distance lines 23 and 24. Looking back at FIG. 3a, fused image pair 26 follows an illusionary plateau from position B to D due to the constant disparity between images 20 and 21. When 20 and 21 cease motions, the disparity disappears and fused image pair 26 appears to terminate movement at real position E.

FIGS. 4a and 4b illustrate the left to right linear unidirectional path of an image pair moving at the different speeds, made up of image 31 (depicted by circled L) seen by the left eye and image 30 (depicted by circled R) seen by the right eye and where the onset of motion of image 30 and 31 is simultaneous. Viewing the motion from above the arrows indicates the image pair moves clockwise as compared to reference clock 25. With onset of movement, fused image 36 appears to move backward from position A to position B due to the disparity produced by the faster speed of image 30 as illustrated in FIG. 4b. Due to the longer duration of movement and the slower speed of left image 31, right image 30 with the faster speed completes the path sooner than image 31 and this is reflected by the diverging lines 33 and 34. Looking back at FIG. 4a, fused image pair 36 follows an illusionary diverging path from position B to E due to the increasing disparity between images 30 and 31 as image 30 pulls further ahead of image 31 with time. When 30 and 31 abruptly cease motions, the disparity disappears and fused image pair 36 appears to move directly to real position F. FIG. 5, schematic 40 represents the back-and-forth oscillation of an image pair where the real path is in a straight line along A-D and by introducing an onset delay of the left image of the image pair, the illusionary clockwise path A-B-C-D-E-F-A follows a rectangular shape. In schematic 41, the speed of the images of the image pair differs, the left image traveling slower than the left right image of the image pair. The real path of oscillation is in a straight line along A-F, the illusionary clockwise path A-B-C-D-E-F-G-H-1-J-A follows a rhombus shape. Interposing a time delay in addition to adjusting speed of images provides more options for tuning disparity to achieve the desired path and degree of motion-in-depth. When "ease in and out" acceleration animation functions of computer presentation programing is applied to each motion segment, the rectangular path of delayed movement disparity (schematic 40) and the rhombus shaped path of different speed disparity (schematic 41) converts the paths into oval illusionary paths as illustrated in schematic 42 of FIG. 5 and mimics the accelerating and decelerating smooth oscillations of a real pendulum. When applying (1) delay of movement, (2) a speed difference between images of image pairs in motion and/or (3) accelerating and decelerating functions to create 3D effects, movements do not need to complete the to-and-fro cycle as in FIG. 5 but can propel an animated image pairs in a linear path, curve or circuitous path.

In FIG. 6 are the left helicopter 70 and right helicopter 71 that form a stereo pair when fused and when animated, the fused helicopter pair appears to rise straight up on takeoff and travel from left to right with inclining stereo depth and achieves a vertical landing, made possible by a hybrid of delay and speed disparities. Helicopters 70 and 71 follows a path having 0.5 second delay and 1.0 second longer duration (speed) for the flight of helicopters 71. Speed and delays can vary if disparities are within the fusible range. As seen in FIG. 3a a delay related disparity animation yields a rectangular shaped path, in FIG. 6 the delay of 0.5 seconds between helicopters 70 and 71 program is responsible for dotted-line (rectangle 73) portion of the stereo depth. As seen in FIG. 3b, a speed related disparity follows a triangular shaped path, in FIG. 6 the 1.0 second longer flight of helicopter 71 is responsible for inclining solid-line 74 above the square. Together, delay and speed disparities give the illusion of a typical helicopter flight with inclining stereo depth during flight and vertical takeoff and landing.

In FIG. 7 are the left airplane 80 and right airplane 81 that form a stereo pair when fused and when animated the fused airplane appears to takeoff in an inclining path due to speed disparity and lands in a smooth declining path due to ease out function. Fused image pair (airplanes 80 and 81) follow a path having 0 delay and 1.0 second longer duration (slower speed) for the flight of airplane 81. As seen in FIG. 3b speed related disparity animation follows a triangular 7 shaped path and ease out function smooths the truncated ending of speed disparity. Together, speed disparity and ease out function give the illusion of a typical of airplane flight with inclining stereo depth path 83 during flight and smooth declining stereo depth 84 during landing.

Conversion of a two-dimensional movie into a rich three-dimensional experience is provided by delaying the start of one of a pair of identical movies being viewed through a stereo viewer. FIG. 8 illustrates a graphic presentation of two identical film frames (61a and 61b) of a two-dimensional movie capturing jelly fish swimming in an aquarium that fuses to form mental perception 62 when viewed by the right and left eyes of a subject. When the movie is viewed while the right and left frames are synchronized, the subject sees jelly fish swimming in two dimensions, however, delaying one of the movies, the fused images display rich 3-dimensional movement of only those images in motion. Associating additional image pairs of different positional disparities moving in more than one layer provides even a more robust three-dimensional experience for vision therapy and entertainment. Turn now to FIG. 9, an additional image pair, fish 60a and fish 60b, is layered in front of the right and left jelly fish movies 61a and 61b, that is, fish 60a is layered in front of movie 61a and fish 60b is layered in front of movie 61b. Animating fish 60a and 60b such that their movements are asynchronous as to speed of movement or delay of movement, provides a visual perception of 3-dimensional fish 63 swimming through 3-dimensional jelly fish 62 swimming for therapeutically stimulating the binocular visual system or entertainment. Images other than jelly fish can be used and more than one image pair can be layered in front of the movies playing in the background.

The preferred means for displaying my invention consists of a stereo viewer housing an electronic display device having (1) a viewable screen capable of displaying still and motion presentations and movies, (2) capacity of processing animation presentations, (3) data storage and (4) hyperlinking capability. A smart phone, iPad, and a computer are among suitable devices. Alternative viewing methods include polarizing filter and red-green glasses as described by Hofeldt patent (U.S. Pat. No. 9,560,960 B2).

My method of producing an animation illusional presentation in layers is: (1) capture a movie of moving subject matter, (2) in a presentation program, such as Keynotes (a) insert new slide and (b) insert exact copies of the background movie captured above on the left and right sides of the slide in the correct separation for stereo viewing and delay the start of one of the movies, (3) insert an object in the layer in-front of the one the movies and animate the object along a desired path, (4) copy and paste the animated object into the identical location of the opposite movies and (5) build the animation sequence for image pairs to start "with" each other, chose the desired delay between each image pair and the chose the desired duration of movement of each image of each image pair.

BRIEF DESCRIPTION OF DRAWINGS

FIG. 1. Prior Art, Pendulum movement

Figure 2:
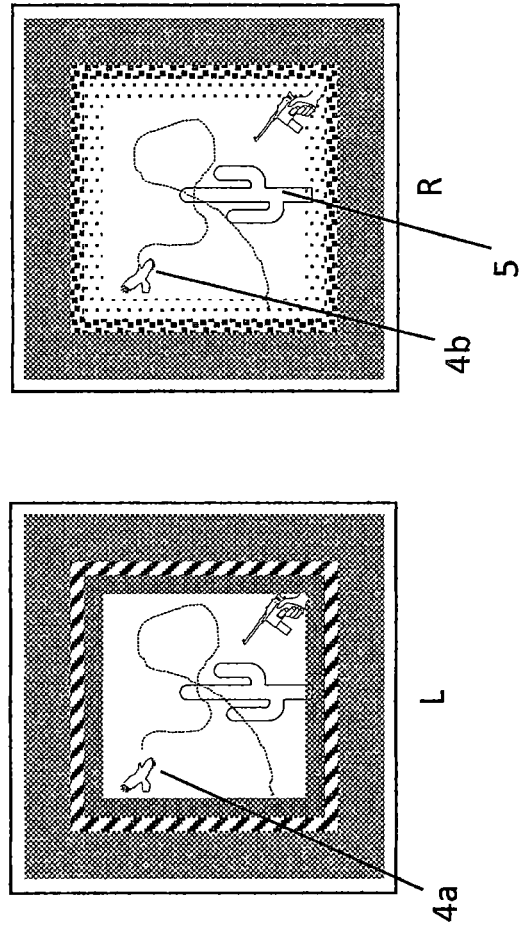
FIG. 2. Prior Art, Hofeldt patent (U.S. Pat. No. 11,007, 109 B1) showing circuitous animation FIG. 3a. Linear unidirectional time-delayed disparity illusionary path FIG. 3b. Linear unidirectional asynchronous speed-disparity illusionary path FIG. 4a. Distance/time graph of time-delayed disparity FIG. 4b. Distance/time graph of asynchronous speed-disparity FIG. 5. To-and-fro movement, with linear animation 40 (delay disparity), 41 (speed disparity) and 42 (ease in and out animation in addition to either delay or speed disparity)
Figure 4A:
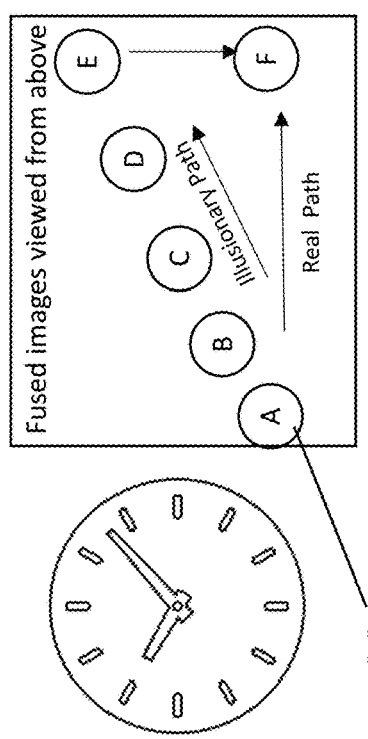
Figure 4B:
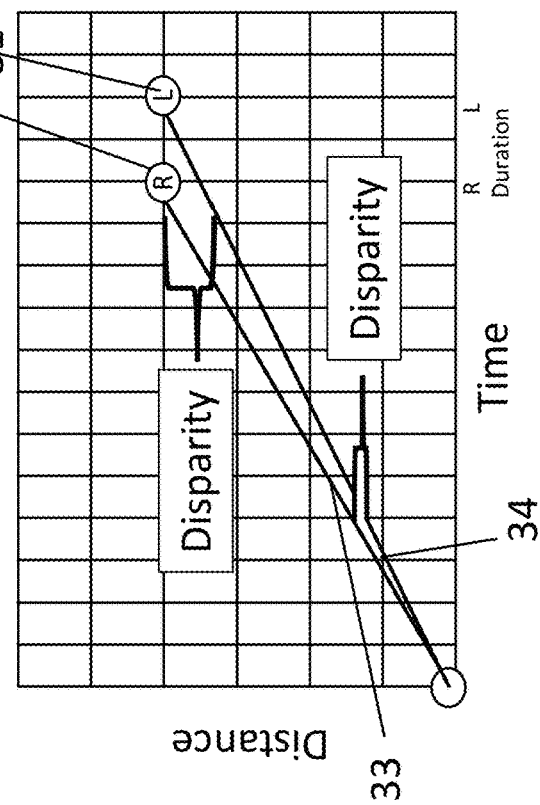
Figure 3A:
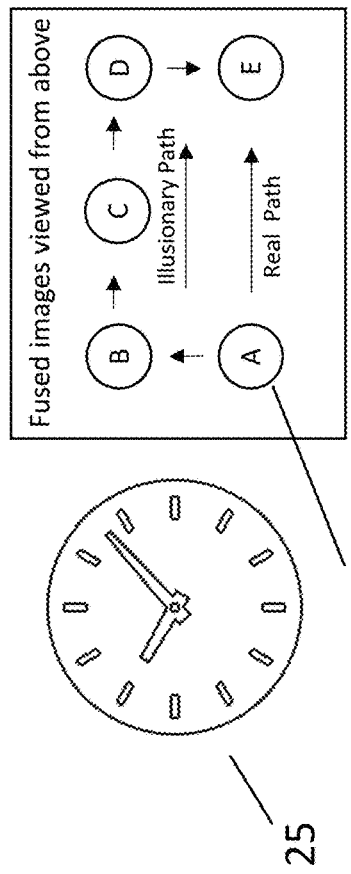
Figure 3B:
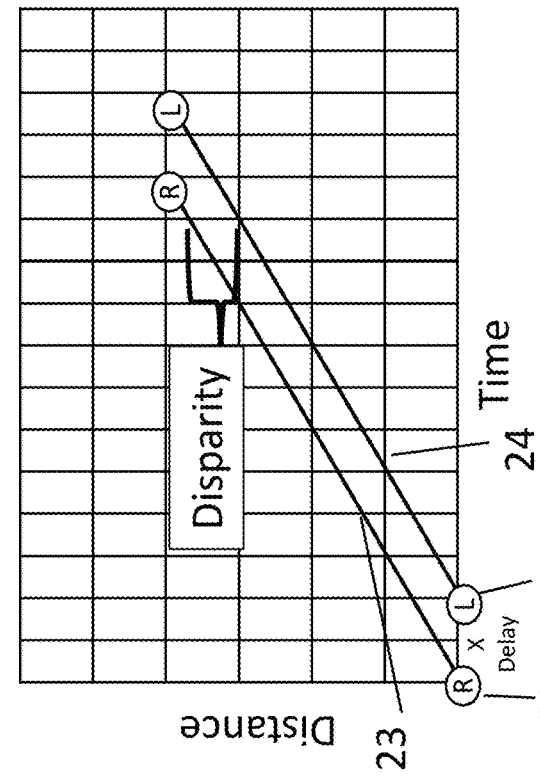
Figure 5:
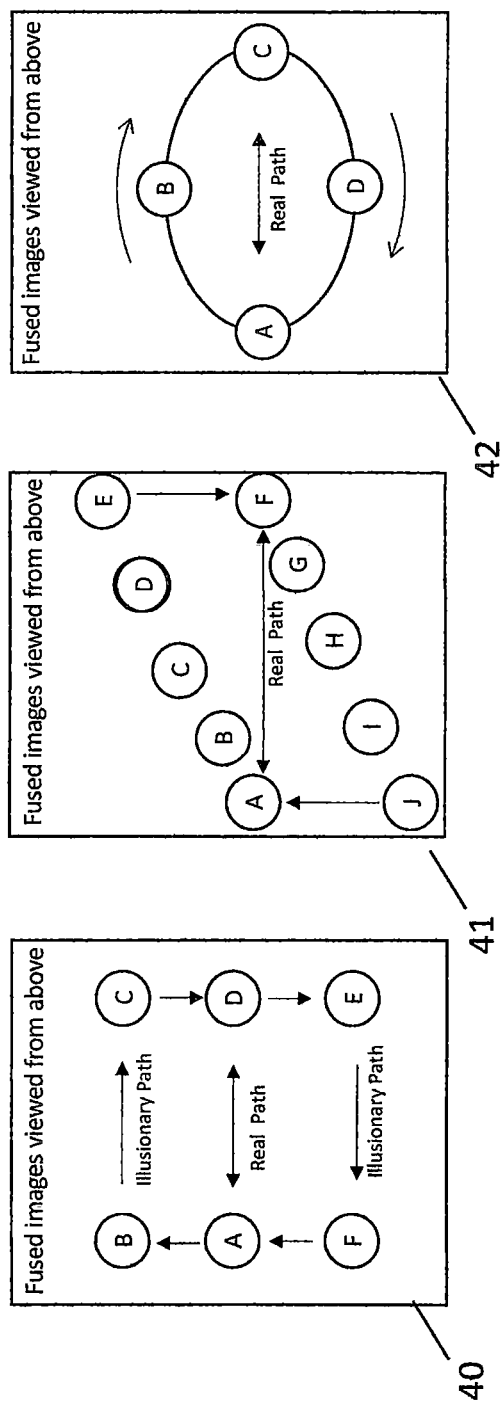
Figure 6:
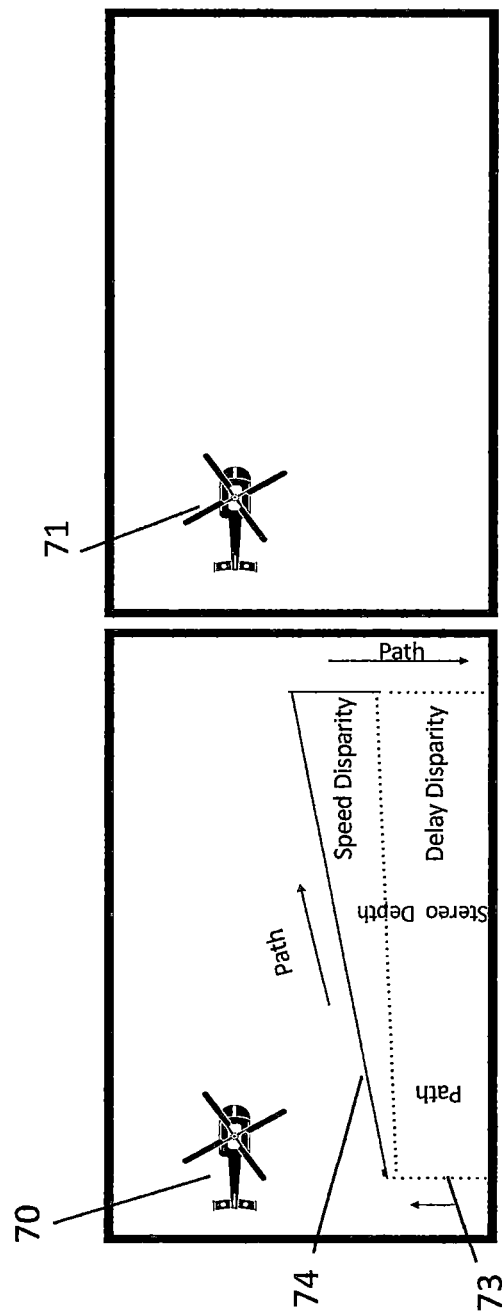
FIG. 6. Depth of stereo illusion of a helicopter image pair due to delay and speed disparities FIG. 7. Depth of stereo illusion of an airplane image pair due to speed disparity and ease out function FIG. 8. Time-delay animation of identical movie frame FIG. 9. Asynchronous animation of the identical movie frame combined with in-front layering of an image pair having asynchronous time delay and/or duration of right and left image movement.
Figure 7:
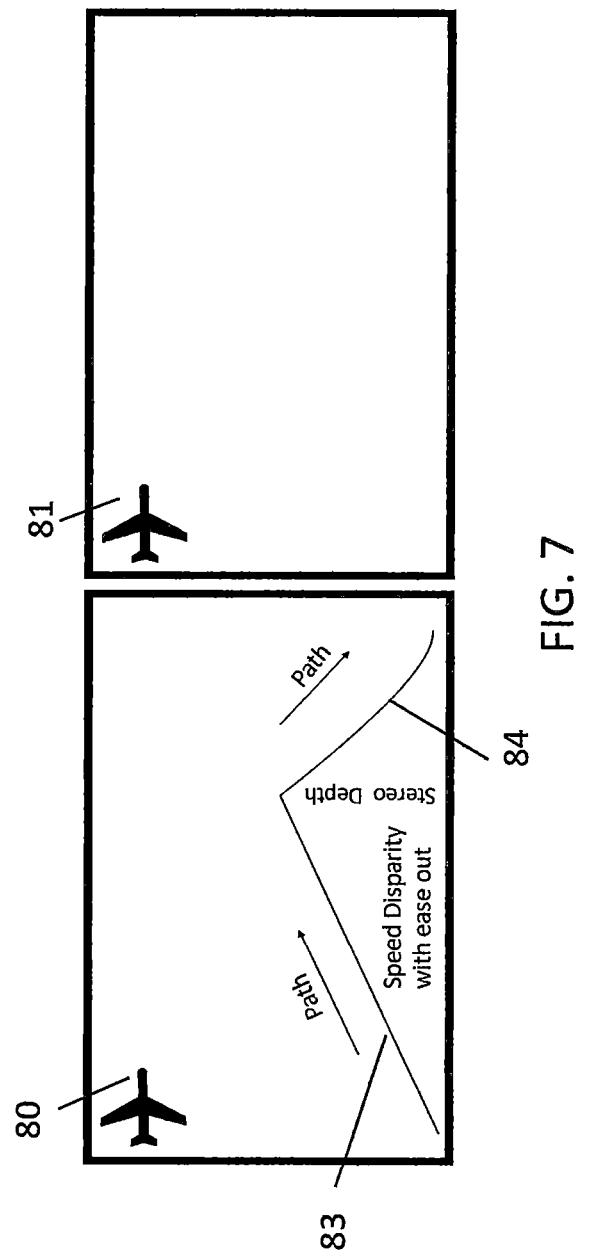
Figure 8:
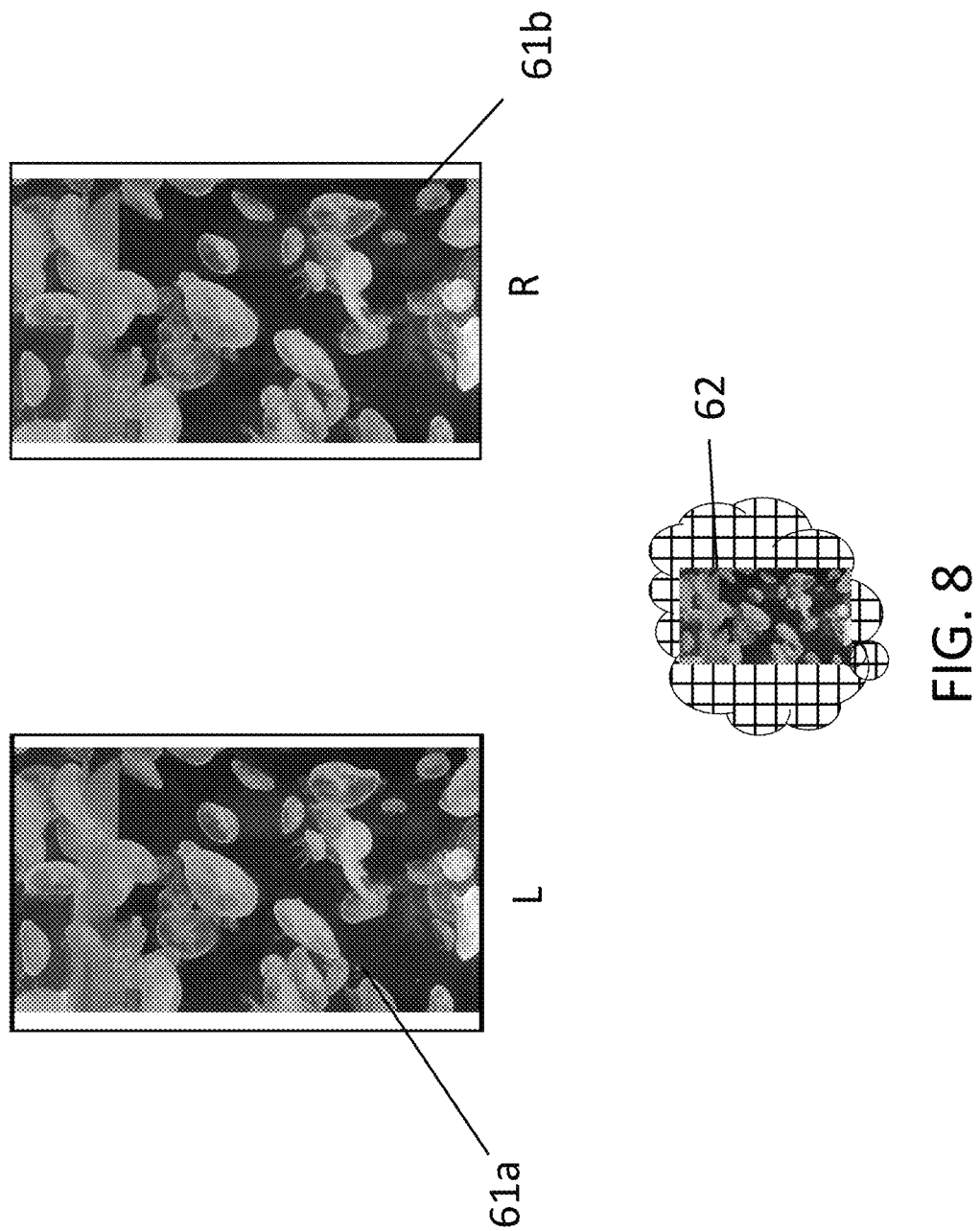
Figure 9:
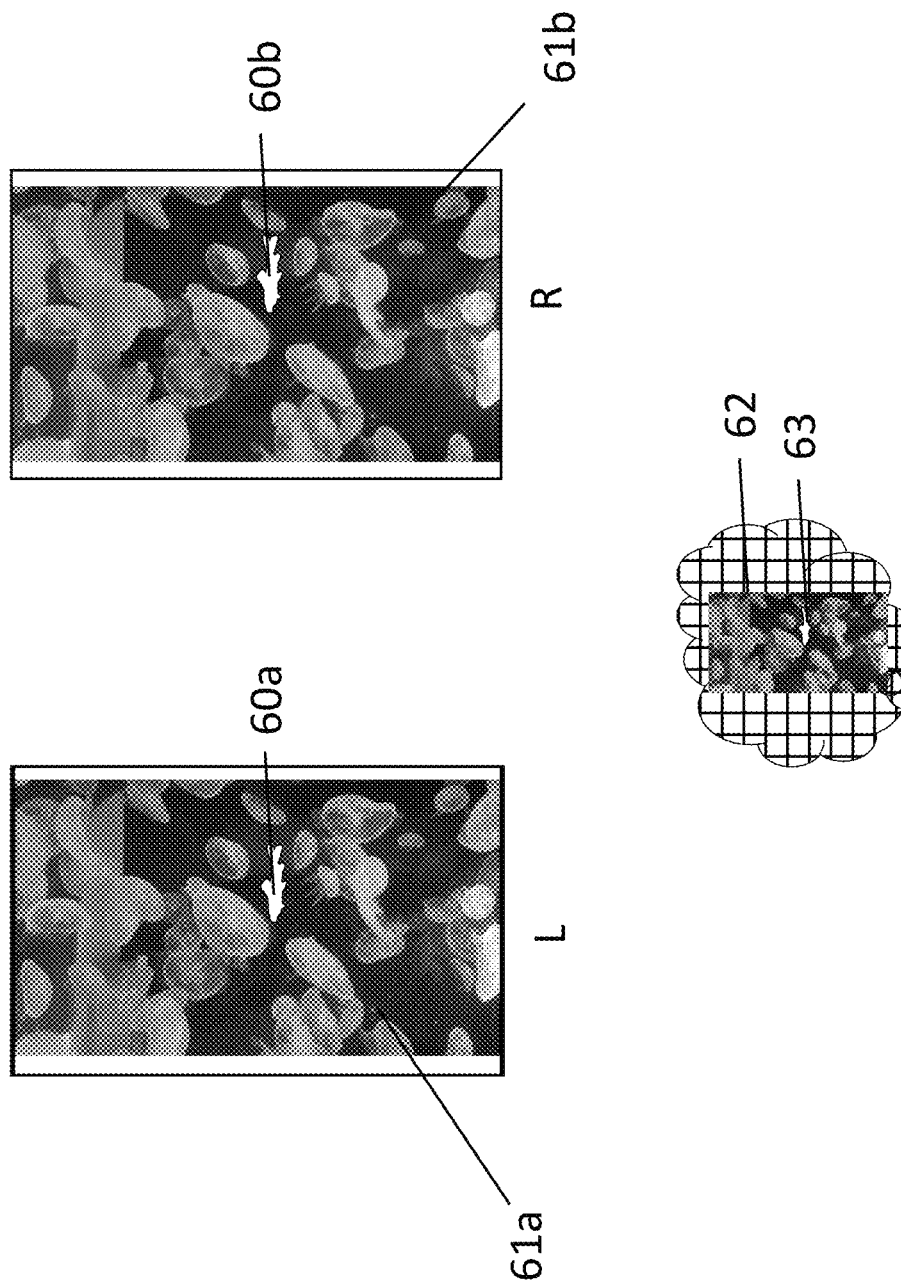

The invention claimed is:

1. A device for active amblyopic therapy or entertainment by stimulation binocular visual pathways with images in motion comprising:
   a stereo viewer, a graphic display device providing a visual space, at least one image pair, the at least one image pair having one image viewed by the right eye and the other image viewed by the left eye and where the images of the at least one image pair travel at different speeds in the visual space.

2. The device of claim 1 where the at least one image pair is moving in the visual space, the movement is back and forth across the visual space and the movement can be linear, curved, or circuitous.

3. The device of claim 1 where movement delay is applied to one image of the at least one image pair travelling at different speeds.

4. The device of claim 1 where an identical reference image pair is positioned in the visual space for viewing the relative stereo depth of the at least one image pair.

5. The device of claim 1 where animation effects of ease in, ease out or easy in and out functions are applied to object movement.

6. A device for active amblyopic therapy or entertainment by stimulation binocular visual pathways by images in motion comprising:
   two identical movies composed of moving subject matter which are viewed binocularly on a graphic display device within a stereo viewer where one of the two identical movies is viewed by the right eye and the other one of the two identical movies is viewed by the left eye where the two identical movies are playing concurrently after one of the two identical movies is delayed starting, and where the disparity of the two identical movies is within the limits of binocular fusion.

7. The device of claim 6 further comprising:
   at least one image is layered over the two identical movies,
   one image of the at least one image pair is layered over the movie in the right side of the stereo viewer and the other one image of the at least one image pair is layered over the movie in the left side of the stereo viewer and where the images of the at least one image pair are moving at different speeds.

8. The device of claim 6 further comprising:
   at least one image pair is layered over the two identical movies,
   one image of the at least one image pair is layered over the movie in the right side of the stereo viewer and the other one image of the at least one image pair is layered over the movie in the left side of the stereo viewer, where the images of the at least one image pair are moving at different speeds and one image of the at least one image pair is delayed.

9. The device of claim 7 where animation of ease in, ease out or easy in and out are applied to object movement.

10. The device of claim 8 where animation effects of ease in, ease out or easy in and out are applied to object movement.

* * * * *